US006687331B1

United States Patent
Muller et al.

(10) Patent No.: US 6,687,331 B1
(45) Date of Patent: Feb. 3, 2004

(54) METHOD AND DEVICE FOR MAKING RADIOGRAPHIC IMAGES

(75) Inventors: Serge Muller, Guyancourt (FR); Jean-Pierre Saladin, Bagneux (FR); Luc Miotti, Vanve (FR)

(73) Assignee: GE Medical Systems SA, Buc (FR)

( * ) Notice: Subject to any disclaimer, the term of this patent is extended or adjusted under 35 U.S.C. 154(b) by 0 days.

(21) Appl. No.: 09/450,917

(22) Filed: Nov. 29, 1999

(30) Foreign Application Priority Data

Nov. 27, 1998 (FR) .............................. 98 14977

(51) Int. Cl.⁷ ................................ H05G 1/64
(52) U.S. Cl. ........................ 378/98.5; 378/95
(58) Field of Search ................... 378/98.5, 195–197

(56) References Cited

U.S. PATENT DOCUMENTS

| 3,916,192 A | * | 10/1975 | Schmitmann | 378/116 |
| 4,049,967 A | | 9/1977 | Berger et al. | 250/445 |
| 4,433,429 A | * | 2/1984 | Finkenzeller et al. | 378/98.5 |
| 4,937,848 A | | 6/1990 | Horbaschek et al. | 378/99 |
| 5,155,757 A | * | 10/1992 | Sakaniwa et al. | 378/196 |
| 5,224,147 A | | 6/1993 | Collin et al. | 378/162 |
| 5,539,798 A | | 7/1996 | Asahina et al. | 378/98.5 |

FOREIGN PATENT DOCUMENTS

DE 2850410 5/1980

* cited by examiner

Primary Examiner—Craig E. Church
(74) Attorney, Agent, or Firm—Jay L. Chaskin; Cantor Colburn LLP

(57) ABSTRACT

Device for taking radiologic images, of the type comprising a means of emission of an X-ray beam and a means of reception of the X-ray beam after it has passed through an organ to be studied. The means of emission and the means of reception are supported by an arm pivoting about at least one shaft supported by a frame. The device comprises a means for detecting the angle of swivel of the arm, a means for entering data relative to the organ to be studied, a processing means capable of determining the type of image that will be taken as a function of the angle of swivel and of the said data relative to the organ, and a means for displaying on the image the type of image determined by the said processing means.

18 Claims, 4 Drawing Sheets

METHOD AND DEVICE FOR MAKING RADIOGRAPHIC IMAGES

BACKGROUND OF THE INVENTION

The present invention relates to the field of radiology designed for study of the human body in general and of certain organs in particular, such as the breasts, the heart, the circulatory system, etc.

In conventional fashion, an X-ray machine comprises an X-ray tube capable of emitting a beam of X-rays along a given axis, an X-ray receiver arranged on the path of the X-ray beam, the organ to be studied being interposed between the X-ray tube and the receiver, and a support of the X-ray tube and the receiver capable of displacing them along at least one axis, for the purpose of obtaining the desired positioning with respect to the organ to be studied.

The X-ray machine comprises, in addition, a supply of electric energy designed for the X-ray tube and possibly with various motors or electric actuators, and an X-ray tube control making it possible to obtain appropriate adjustments.

The X-ray receiver is provided with a film, capable of being acted on by X-rays, which is developed after the taking of images. An X-ray detector of digital type may alternatively be used, making it possible to visualize the image obtained on a video screen and/or to print it.

To analyze a radiograph so obtained, it is essential to know the relative position of the patient or of the organ, and of the X-ray tube/receiver assembly at the time of taking of the image. For this purpose, a marker with letters made of lead is used, which is arranged on the path of the X-rays, for example on the receiver, so that the radiograph bears the mark of these letters of lead. This marking by letters is done by using standardized abbreviations, making it possible to describe whether the left or right part of the patient's body has been radiographed, the use of an enlargement and the angle of projection, or any other datum facilitating interpretation of the radiograph.

Positioning of these letters made of lead is done by an operator before the radiographic image is taken. The operator might commit errors presenting serious disadvantages. For example, in the case of mammography, an error in side may lead to performing a biopsy not on the breast presenting micro-calcifications or other symptoms, but on the other breast not presenting any of these symptoms.

BRIEF SUMMARY OF THE INVENTION

The present invention is to reduce the possibility of errors in the marking of a radiograph. The present invention is to automate the marking of a radiograph.

The device for taking radiologic images is of the type comprising a means of emission of an X-ray beam and a means of reception of the X-ray beam after it has passed through an organ to be studied. The means of emission and the means of reception are supported by an arm pivoting about at least one shaft supported by a frame.

The device for taking radiologic images comprises a means for detecting the angle of swivel of the arm, a means for entering data relative to the organ to be studied, a processing means capable of determining the type of image that will be taken as a function of the angle of swivel and of the said data relative to the organ, and a means for displaying on the image the type of image determined by the processing means. The operator is thus relieved of a certain number of repetitive tasks for which an error is liable to be produced.

Advantageously, the means for detecting the angle of swivel of the arm comprises a pendulum mounted rotary on the arm and coupled to a rotary potentiometer, rotation of the pendulum with respect to the arm producing rotation of the potentiometer and a proportional variation in the output voltage of the potentiometer. Thus, the means of detection of swivel may be mounted on an existing unit with only small modifications. To dampen the oscillations of the pendulum, an electromagnetic brake may be provided. A reading of the angle may thus be made very quickly after the end of the motion of the arm. A means may likewise be provided for converting the output voltage of the potentiometer into a digital variable furnished to the processing means.

An embodiment of the present invention is a method for generating images from an apparatus for taking radiologic images, of the type comprising a means of emission of an X-ray beam and a means of reception of the X-ray beam after it has passed through an organ to be studied, in which:

the angle between the axes of the X-ray beam and a reference axis, for example the principle axis of the human body or the vertical, is measured;

data relative to the organ to be studied are entered;

the type of image that will be taken is determined as a function of the angle and the data; and the type of image that has been determined is displayed on the image.

Thus, the operator need no longer identify the type and the direction of an image, which makes for an appreciable savings of time, reducing labor costs and permitting optimal use of the X-ray machine.

In one embodiment of the invention:

the criteria of rotation and tilting of the image are input as function of the type of image;

after rotation and/or tilting images are displayed in accordance with the said criteria.

Display may alternatively be effected either according to rules specified

BRIEF DESCRIPTION OF THE DRAWINGS

The present invention will be better understood upon reading of the detailed description of one embodiment taken by way of example, not at all limitative, and illustrated by the accompanying drawings, wherein.

DETAILED DESCRIPTION OF THE INVENTION

Figure 1:
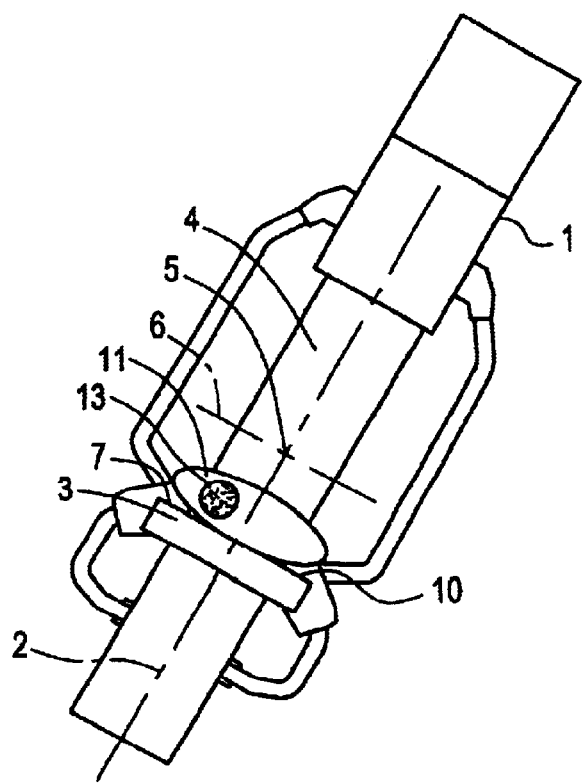
FIG. 1 is a schematic front view of an X-ray machine in a first position.

In FIG. 1, the x-ray machine comprises an X-ray tube 1 capable of emitting an X-ray beam centered on an axis 2. On the path along which the X-rays are propagated and centered on the axis 2, there is arranged a receiver 3 capable of converting the incident X-rays into an electronic signal. The receiver 3 may be provided with an X-ray detector of the solid state type. The tube 1 and the receiver 3 are each supported at an opposite end of an arm 4 supported by a frame, not represented, and mounted rotary with respect to the frame about an axis 5 perpendicular to the plane of the figure and which passes through the intersection of the axis 2 and the axes labeled 6, these three axes being mutually perpendicular. The arm 4, the tube 1 and the receiver 3 may be turned through a complete turn with respect to the frame.

An X-ray machine with one axis has been represented in FIG. 1.

Of course, the present invention applies also to multiple-axis radiology apparatus, for example with a C-shaped arm with three axes or four axes.

The X-ray detector of the receiver 3 is provided with a sweep system for the reading of the matrix of elementary detection cells constituting the said detector.

Figure 2A:
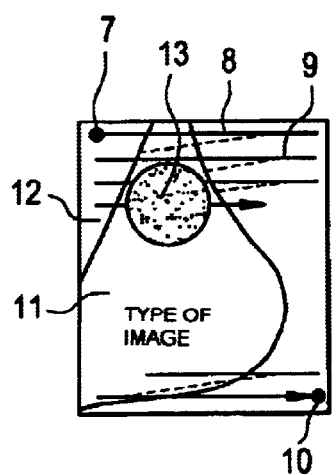
FIGS. 2a and 2b are schematic representations of the view obtained with the apparatus of FIG. 1.
Figure 2B:
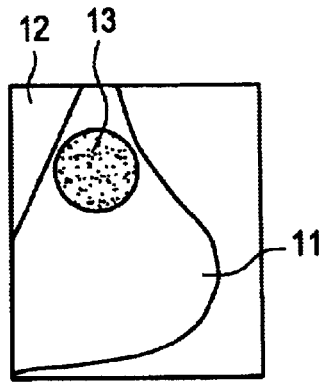

As can be seen in FIG. 2a, reading of the detection cells is effected in successive fashion beginning with the point labelled 7, which is situated at the top and at the left-hand side of the image, then continuing toward the right with the cells of the line 8 to which the point 7 belongs. Having arrived at the right-hand end of the line 8, reading continues with the cell farthest at the left of the following line 9, and so on to the point 10 farthest on the right of the last line below the image. This kind of sweep thus makes it possible to see, in the case of mammography, the breast 11 of a patient and a part of her pectoral muscle 12, and to distinguish the glandular zone 13 of the breast 11, which has been represented in the form of a circle.

Figure 3:
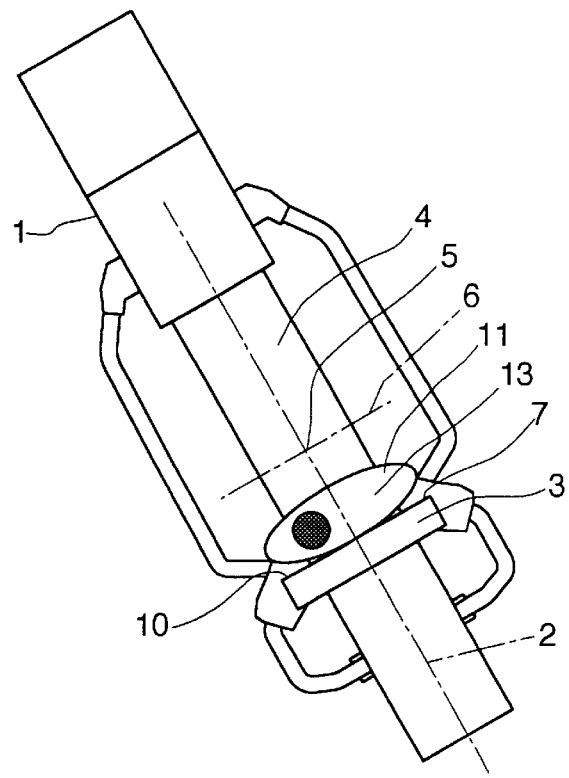
FIG. 3 is a schematic front view of an X-ray machine in a second position.
Figure 4A:
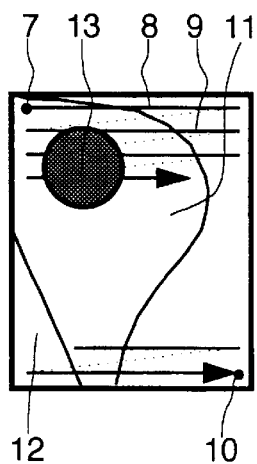
FIGS. 4a to 4c are schematic representations of the view obtained with the apparatus of FIG. 3.
Figure 4B:
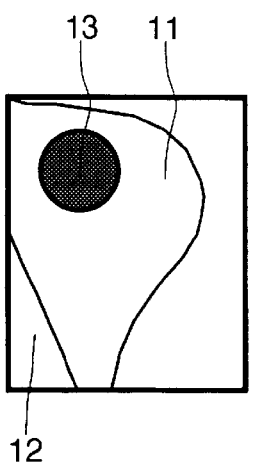
Figure 4C:
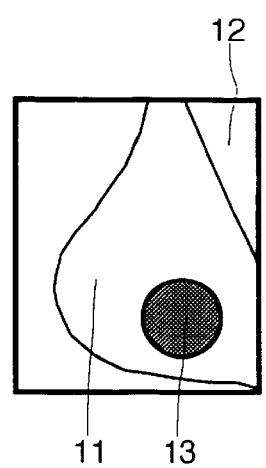

In FIG. 1, the point 7 is arranged higher than the point 10. As a result, the image obtained directly by the reading of the matrix of cells of the detector of the receiver 3 is arranged in the right direction. This is not the case when the image is taken in the position illustrated in FIG. 3, where the point 7 is located lower than the point 10, which results in an reversed image (FIGS. 4a and 4b) because of the sweep reading, which is always effected beginning with the point 7, line by line, and ending with the point 10. A reversed image is thus obtained, where the bottom of the breast is located at the top of the image and the top of the breast is located at the bottom of the image. It is therefore necessary to effect a conversion of the image by rotation about an axis perpendicular to the plane of the image, in order to find a useful image.

The user may wish to convert the image by rotation about an axis arranged in the plane of the image and parallel to its long sides. As a matter of fact, standards for visualization of film images in mammography do exist. For example, it has been agreed to look at an LMLO view in such a way that the pectoral muscle is located at the left and the nipple at the right. In the same way, it has been agreed to look at an RMLO view so that the pectoral muscle is situated at the right and the nipple at the left. However, even if this convention is the one most commonly used, other conventions characteristic of users exist. In particular, a certain number of users prefer to look at images in a way contrary to what is most commonly used. In that case, it is advisable to apply a rotation about an axis arranged in the plane of the image and parallel to its long sides. Thus, two standards may be distinguished, according to which this conversion must be applied for none of the views or for every view. The possibility of the user's making a choice to apply or not to apply this conversion for only certain of the views may alternatively be envisaged.

Figure 5:
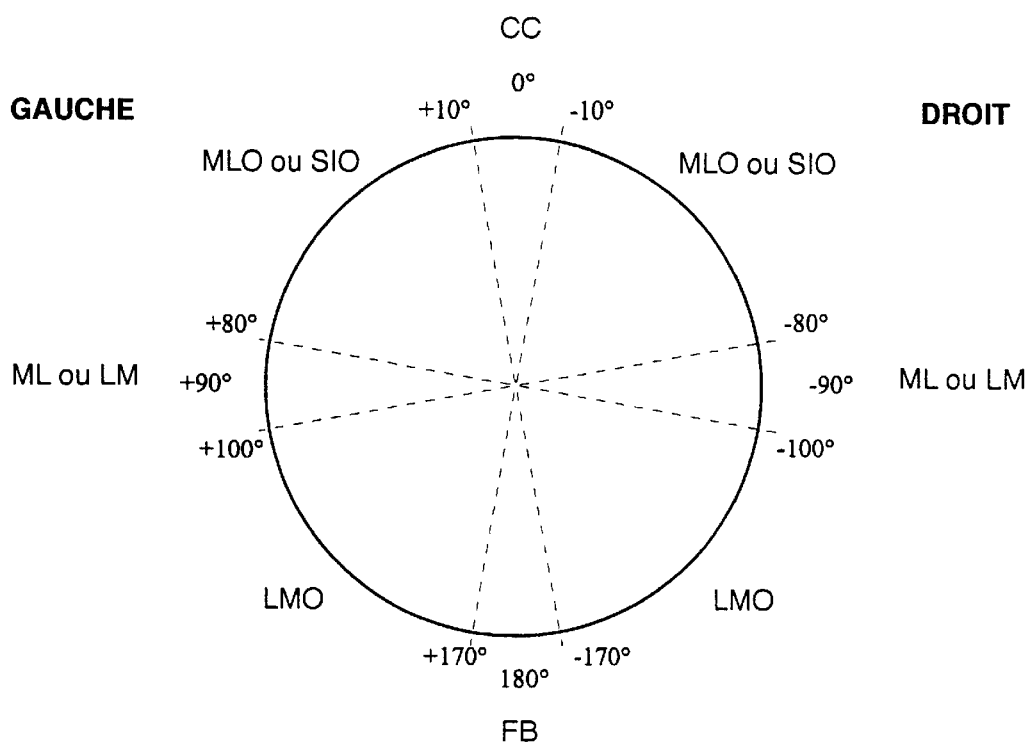
FIG. 5 is a diagram showing the abbreviations used for naming the view as a function of the angle of the arm.

FIG. 5 shows the various names of views taken as a function of the angle of inclination of the arm. If the angle is between −10 and +10°, the view will be called craniopodal or craniocaudal, CC in abbreviated form. In this view, the receiver is arranged at the lower side of the breast. When the angle is between +10° and +80° or between −10° and −80°, the view is called outer or medio-lateral oblique profile, MLO in abbreviated form, the receiver there still being arranged against the lower outer face of the breast. The view may likewise be called superolateral-inferomedial, SIO in abbreviated form, the inner lower face of the breast being arranged against the receiver. When the angle is between +80° and +100° or −80° and −100°, the view is called strict outer profile or strict inner profile, or medio-lateral or lateromedial, according to whether the outer face or the inner face of the breast is arranged against the receiver.

When the angle is between +100° and +170°, −100° and −170°, the view is called inner profile or lateromedial oblique, the inner upper face of the breast being arranged against the receiver. When the angle is close to 180°, between +170° and −170°, the view is called podocranial or caudocranial, FB in abbreviation, the upper face of the breast being arranged against the receiver.

Lastly, other abbreviations are used for particular views. For example, the view is called exaggerated craniocaudal, XCCM in abbreviation, when for the craniocaudal view the patient is turned 45° with the inner face of the breast close to the detector. This same view is called XCCL when the patient is turned 45° with the outer face of the breast close to the detector. It is possible to take views with the lower face of the two breasts against the receiver, this view being designated by the abbreviation CV. Finally, the view designed to take the axillary part of the breast is termed AT.

These abbreviations may be supplemented by an abbreviation relative to the laterality of the organ studied, information relative to enlargement and, if applicable, to the enlargement factor and supplementary information, particularly in case of the presence of a breast implant that it is sought to shift out of the field of view toward the thorax, abbreviation ID, in case of taking a view involving a part very close to the skin, of tangential type, abbreviation TAN, and in case of rotation of the breast between the compression pad and the receiver, in the outer direction, abbreviation RL, or in the inner direction, abbreviation RM, and lastly in case of a compression spot requiring a special compression pad, abbreviation S and designed for the visualization of a particular localized zone.

In practice, the views CC and FB are taken around 0° and 180° respectively. Angles close to 0° are rarely used, save for views of type XCCL, and XCCM.

Naturally, the possibility of adjusting the angular limits between the various types of views in a way different from those illustrated in FIG. 5 will be left up to the operator.

Figure 6:
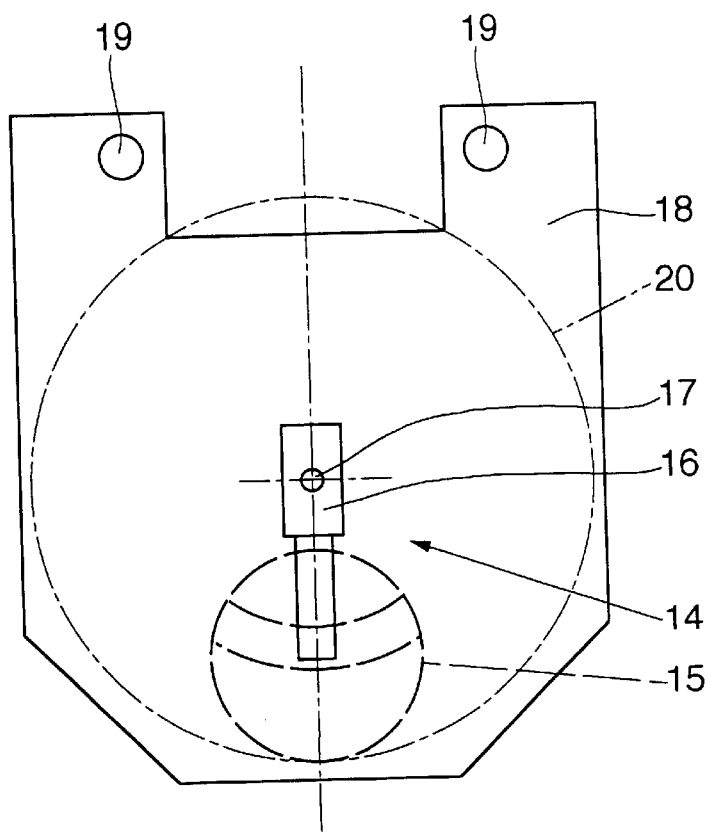
FIG. 6 is a front view in elevation of the pendulum mounted in the arm of the X-ray machine.

As can be seen in FIG. 6, the arm of the radiology apparatus is equipped with a pendulum 14 formed by a weight 15 and an arm 16 making it possible to suspend the weight 15, the arm 16 being articulated about an axis 17 parallel to the axis 5 of FIG. 1.

The pendulum 14 is supported by a base plate 18 fixed to the arm of the apparatus and can thus be made available in the form of a kit capable of being mounted in or on the arm 4 (FIG. 1) without any modification other than that required for its fixation, for example, by means of screws, not represented, passing into the holes 19 of the base plate 18. The pendulum 14 is capable of turning 360° with respect to the plate 18, describing the circle 20 represented in a dash-dotted line.

A potentiometer, not represented, is fixed on the plate 18. The potentiometer comprises a fixed member and a movable part serving to control it. The movable part is fixed in rotation with the pendulum 14, so that the rotation of the pendulum 14 drives the rotation of the control part of the potentiometer and therefore modifies the value of the resistance of the potentiometer in a way corresponding to the angle between the pendulum 14 and the arm of the radiology device.

Figure 7:
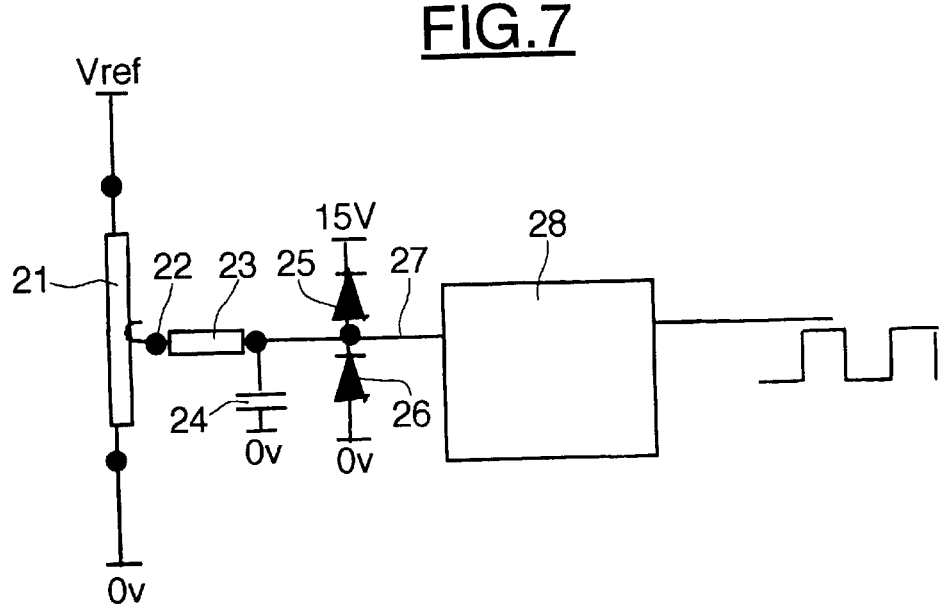
FIG. 7 is an electronic diagram showing processing of the information coming from the pendulum.

FIG. 7 illustrates an example of the electronic circuit that may be arranged at the outlet of the potentiometer. The potentiometer 21 is supplied by a reference voltage, its opposite terminal being grounded. The third terminal 22 of the potentiometer 21 is connected to filtering means comprising a series resistance 23, a parallel capacitor 24 and diodes 25 and 26 connected to a positive feed voltage and to ground respectively.

The output 27 of the filtering means is connected to an analog/digital converter 28 capable of emitting an output signal, for example a notched signal, of a frequency proportional to the input voltage. Thus, a counter, not represented, arranged at the output of the analog/digital converter 28, can compare the signal received from the converter 28 with a clock signal and derive from it the value of the angle between the arm and the pendulum that always remains vertical, hence between the arm and the vertical.

The pendulum 14 preferably will be equipped with an electromagnetic brake, not represented, which will allow it to stabilize quickly at the end of a motion of rotation of the arm, so that a reading of the angle may be effected in precise fashion shortly after displacement of the arm, preferably less than four seconds after the end of displacement.

After reading of the angle of the arm, it is compared, by way of a processing means such as an electronic calculator, with prerecorded threshold data such as those illustrated in FIG. 5, to derive from them information relative to the types of views. The angle of the arm may alternatively be displayed on the screen.

For certain kinds of views, compression pads of a special type are used. By compression pad is meant the device transparent to X-rays, arranged on the path of X-rays between the X-ray tube and the receiver, and serving to compress the breast between the pad itself and the receiver. The standard compression pad is used for taking views of type CC, FB, MLO, LMO, ML, LM and SIO. By contrast, views of type AT, designed for visualization of the part of the breast closest to the axilla, need a special compression pad that replaces the standard pad. Views of type S, designed to take very localized zones of the breast, likewise need a special compression pad.

Compression pads are equipped with pins provided to cooperate with corresponding holes of the arm for their fixation. At least one pin of each compression pad may advantageously be equipped with coding means, for example in the form of three magnets bearing information on three bits and thus capable of coding eight different signals corresponding to at most eight different types of compression pads. The corresponding holes of the arm are provided with sensors, for example in the form of magnetic reed-type relays capable of detecting the magnets and provided for transmitting information relative to the compression pad to the processing system. In this way, the risk of an operator making a mistake when he indicates on a keyboard or on some other entry means either the type of compression pad used or the type of view that will be taken is eliminated.

The invention thus make it possible to greatly reduce the information that must be indicated by the operator, conventionally by means of letters made of lead. The presence of the pendulum, as well as of an optical angle transmitter sensing the angle of swivel of the arm with respect to the frame, makes it possible to determine most types of views, and whether or not the image must be rotated. The detection means associated with compression pads and their support holes make it possible to provide data regarding types of views, particularly in the case of special AT or S-type views.

Use of an enlargement and the enlargement factor may alternatively be furnished to the processing means in automatic fashion by the enlargement platform that is provided on the radiology device for this purpose. The operator need only indicate by means of his control keyboard or by any other entry means, of which breast, left or right, a view is to be taken. For greater safety, it may be provided that emission of the X-ray beam is precluded so long as the information relative to the laterality of the breast has not been indicated to the processing means of the radiology device.

By way of example, the table below illustrates the various types of views as a function of the angle, as well as the various types of rotations of the image as a function of the angle and of the laterality of the breast. In the column "Name of view," the first letter is relative to the laterality of the breast, L for the left breast, R for the right breast. For columns 3 and 4, rotation is a rotation about an axis perpendicular to the plane of the view, and tilt is a rotation about an axis arranged in the plane of the view and parallel to its long sides.

Then, a display of images according to the standard most commonly used in mammography is obtained. A variant could be to permit a tilt for all the views, which would correspond to another way of displaying mammography images that is presently utilized by some users. It is also quite possible for a user to define his own list of views to which he wishes a tilt of the images to be applied before their display.

| Name of view | Min angle | Max angle | Rotation | Tilt |
| --- | --- | --- | --- | --- |
| LCC, LXCCM, LXCCL, CV | −10° | +10° | No | No |
| RCC, RXCCM, RXCCL | −10° | +10° | Yes | No |
| LMLO, LAT, RSIO | −80° | −10° | No | No |
| LML, RLM | −100° | −80° | No | No |
| RLMO | −170° | −100° | No | No |
| RLMO, RAT, LSIO | +10° | +80° | Yes | No |
| RML, LLM | +80° | +100° | Yes | No |
| LLMO | +100° | +170° | Yes | No |
| LFB | −170° | +170° | No | No |
| RFB | −170° | +170° | Yes | No |

The present invention makes it possible to considerably reduce the risk of error in naming of a radiograph and the consequences that may result from this, while at the same time reducing the work load of the operator, and this by means of minimal modifications of the radiology apparatus. In the case of mammography, the great majority of views may be taken indicating only the side of the breast to be radiographed. Only a few special views will require the entry of supplementary information by the operator.

In another embodiment of the invention, the means for detecting the angle of swivel of the arm comprises an angle transmitter sensing the angle of swivel of the arm with respect to the frame. The angle transmitter may be of the optical type.

In one embodiment of the invention, the device for taking radiologic images comprises a support for a compression pad, the support being in one piece with the arm, and a means for detection the type of compression pad used. the means being connected to the processing means.

Advantageously, the device for taking radiologic images comprises a means capable of returning the image by rotation about an axis perpendicular to the plane of the image and/or by rotation about an axis contained in the plane of the image.

Of course, the invention will serve for the naming of other organs such as the heart, the brain, the circulatory system of such and such region of the body, etc. Once the name of the view has been determined, it may be displayed on the screen, displayed on the screen with the radiograph, printed with the radiograph or else sent to a flash device designed to expose a conventional radiologic film.

Various modifications in the structure and/or function and/or steps of the disclosed embodiments may be made by one skilled in the art without departing from the scope and extent of the invention.

What is claimed is:

1. A device for taking radiologic images, comprising a means for emission of an X-ray beam and a means for reception of the X-ray beam after it has passed through an organ to be studied, the means for emission and the means of reception being supported by an arm pivoting about at least one shaft supported by a frame, comprising:
   a means for detecting the angle of swivel of the arm;
   a means for entering data relative to the organ to be studied;
   a processing means capable of determining the type of the image that will be taken as a function of the angle of swivel and of the data relative to the organ; and
   a means for displaying on the image the type of image determined by the processing means.

2. The device according to claim 1, wherein the means for detecting the angle of swivel of the arm comprises a pendulum mounted rotary on the arm and coupled to a rotary potentiometer, whereby rotation of the pendulum with respect to the arm produces rotation of the potentiometer and a proportional variation in the output voltage of the potentiometer.

3. The device according to claim 2, comprising an electromagnetic brake for damping the oscillations of the pendulum.

4. The device according to claim 2, comprising a means for converting the output voltage of the potentiometer into a digital variable furnished to the processing means.

5. The device according to claim 3, comprising a means for converting the output voltage of the potentiometer into a digital variable furnished to the processing means.

6. The device according to claim 1, wherein means for detecting the angle of swivel of the arm comprises an angle transmitter sensing the angle of swivel of the arm with respect to the frame.

7. The device according to claim 5, wherein the angle transmitter is of the optical type.

8. The device according to claim 1 wherein, comprising a support for a compression pad, the support being in one piece with the arm, and a means for detecting the type of compression pad used, the said means being connected to the processing means.

9. The device according to claim 1, comprising a means capable of returning the image by rotation about an axis perpendicular to the plane of the image and/or by rotation about an axis contained in the plane of the image.

10. A method for generation of images from an apparatus for taking radiologic images, of the type comprising a means of emission of an X-ray beam and a means of reception of the X-ray beam after it has passed through an organ to be studied, comprising the steps of:
   measuring the angle between the axis of the X-ray beam and a reference axis;
   entering data relative to the organ to be studied;
   determining the type of image that will be taken as a function of the angle and the data; and
   displaying the type of image that has been determined on the image.

11. The method according to claim 9:
   input criteria of rotation and tilting of image as a function of the type of image; and
   displaying after rotation and/or tilting images in accordance with the criteria.

12. The method according to claim 10 comprising:
   providing a table from which various types of image views may be selected as a function of the angle, the rotation of the images to be taken and the orientation of the organ to be studied; and
   displaying the type of image view selected on a visual monitor or together with the radiologic image or printed with the radiologic image or provided to a conventional radiologic film.

13. The method according to claim 10 wherein the radiologic image is a radiograph.

14. The device according to claim 1 comprising:
   means mounted on the arm coupled to means for determining a signal; and
   means for converting the signal into a signal provided to the means for processing.

15. The device according to claim 1 wherein the radiologic image is a radiograph.

16. A device for providing a radiograph of an object comprising:
   means for emission of an X-ray beam along an axis;
   means for reception of the X-ray beam after it has passed through the object;
   means for providing a signal which is a proportional variation of an angle formed between the means for emission and a reference axis;
   means for providing data from which various types of radiographs may be selected as a function of the angle, a description of the object and an orientation of the object; and
   means for displaying on the radiograph the selected type of image and the data for the selected image.

17. A device for providing radiograph of an object comprising:
   means for emission of an X-ray beam along an axis;
   means for reception of the X-ray beam after it has passed through the object;
   a potentiometer for providing a signal which is a proportional variation of an angle formed between the means for emission and a reference axis;
   a look-up table for providing data from which various types of radiographs may be selected as a function of the angle, a description of the object and an orientation of the object; and
   means for displaying on the radiograph the selected type of image and the data for the selected image.

18. A device for providing radiograph of an object comprising:

means for emission of an X-ray beam along an axis;

means for reception of the X-ray beam after it has passed through the object;

a pendulum rotatively coupled to the means for emission;

a rotary potentiometer coupled to pendulum for providing a signal which is a proportional variation of an angle formed between the means for emission and a reference axis;

a look-up table for providing data from which various types of radiographs may be selected as a function of the angle, a description of the object and an orientation of the object; and means for displaying on the radiograph the selected type of image and the data for the selected image.

* * * * *